United States Patent [19]
Sheridan

[11] Patent Number: 6,086,924
[45] Date of Patent: *Jul. 11, 2000

[54] SKIN CARE COMPOSITION

[75] Inventor: Frank Sheridan, Woodbridge, United Kingdom

[73] Assignee: Stiefel Laboratories (Ireland) Limited, Ireland

[ * ] Notice: This patent issued on a continued prosecution application filed under 37 CFR 1.53(d), and is subject to the twenty year patent term provisions of 35 U.S.C. 154(a)(2).

[21] Appl. No.: 09/101,402

[22] PCT Filed: Jan. 8, 1997

[86] PCT No.: PCT/GB97/00048

§ 371 Date: Jul. 7, 1998

§ 102(e) Date: Jul. 7, 1998

[87] PCT Pub. No.: WO97/25022

PCT Pub. Date: Jul. 17, 1997

[30] Foreign Application Priority Data

Jan. 8, 1996 [GB] United Kingdom .................... 9600278
Dec. 10, 1996 [GB] United Kingdom .................... 9625644

[51] Int. Cl.$^7$ .................................................. A61K 33/00
[52] U.S. Cl. ............................................................. 424/724
[58] Field of Search ..................... 514/887, 859; 424/600, 724

[56] References Cited

U.S. PATENT DOCUMENTS 4,297,348  10/1981  Frazier ..................................... 424/180
4,536,399   8/1985  Flynn et al. .............................. 514/63
4,609,674   9/1986  Gupte ....................................... 514/547
5,057,502  10/1991  Walsh ........................................ 514/54
5,194,250   3/1993  Fairhurst et al. ......................... 424/70
5,618,522   4/1997  Kaleta et al. ............................. 424/60
5,785,977   7/1998  Breithbarth ............................. 424/401

FOREIGN PATENT DOCUMENTS 0 067 913    12/1982  European Pat. Off. .
164716 A2    12/1985  European Pat. Off. .
61-204113 A2  9/1986  Japan .
01143815 A2   6/1989  Japan .

OTHER PUBLICATIONS

STN, File Supplier, Karlsruhe, DE, File XP002030245, *Chemical Abstracts,* vol.107, AN=102684.

*Primary Examiner*—William R. A. Jarvis
*Assistant Examiner*—Vickie Kim
*Attorney, Agent, or Firm*—D. Peter Hochberg; William H. Holt

[57] ABSTRACT

The present invention relates to a method for treating spots and other symptoms of acne and related skins disorders in mammals, which comprises applying to the affected area of the skin of the mammal a non-aqueous composition comprising a dermatologically effective amount of a particulate silica, silica hydrate or precursor thereof. The invention also provides compositions for topical application to the skin which comprise particulate silica, silica hydrate or a precursor thereof in a non-aquous carrier medium.

13 Claims, No Drawings

SKIN CARE COMPOSITION

This application is a 371 of PCT/GB97/00048 filed on Jan. 8, 1997.

The present invention relates to a method and composition, notably to a method for the treatment of acne and a composition for topical application in such a method.

BACKGROUND TO THE INVENTION

Many people suffer from acne and related skin disorders in which the sebaceous glands secrete excessive amounts of oily material and cause localised accumulations of oils in the surface layers of the skin, giving rise to unsightly red spots or areas of skin. In extreme cases, these spots can become infected and cause damage to the skin. For convenience, the term acne will be used herein to denote skin disorders which result from secretions of sebum in the skin whose symptoms include skin rashes and inflammations as well as spots and pimples.

There have been many attempts to provide successful treatment for acne, and many of these have been based upon anti-biotic formulations. However, these are expensive and do not provide immediate and effective treatment.

I have now found that fine particulate silica, notably colloidal or precipitated silica or partial hydrates thereof, is remarkably effective in providing rapid alleviation of the symptoms of acne and related skin disorders, that is the spots, inflammation and red areas of the skin caused by the underlying disorder.

SUMMARY OF THE INVENTION

Accordingly, the present invention provides a method for the alleviation of the symptoms of acne and related skin disorders in mammals, which method comprises applying to the affected area of the skin of the mammal a non-aqueous composition comprising a dermatologically effective amount of a particulate silica, which may be an anhydrous form or a partial hydrate thereof or precursor thereof.

The invention also provides a dermatologically active composition for topical application to the skin of a mammal suffering from acne, which composition comprises a dermatologically effective amount of a particulate silica, which may be an anhydrous form or a partial hydrate thereof or precursor thereof, in an non-aqueous carrier medium.

For convenience the term silica will be used herein to denote silica itself, that is $SiO_2$; partial hydrates of silica, for example those of the formula $Si[SiO]_{2-4}[OH]_{1-2}$; those amorphous materials known as precipitated silica, colloidal silicon dioxide and fumed silica; silicic acid; or silica gel. A particularly preferred form of silica for present use is that fumed silica sold by Degussa AG under the trade mark Aerosil.

The silica for present use may also be used in the form of a precursor thereof, for example a higher hydrate of silica which readily loses water of hydration due to the heat generated during milling to reduce the particle size of the initial material to the desired small particle size so as to form the desired lower hydrate in situ. The term silica is therefore used herein wherever the context permits to include other compounds of silicon, notably the organic derivatives of silicon and the higher hydrates of silica, which form the desired form of silica in situ during the processing of the ingredients to form the compositions of the invention.

For convenience, the invention will be described hereinafter in terms of the use of fine particle size silica.

I believe that the compositions of the invention act by way of removal of fluid from the affected area of the skin causing the fluid secretion in the skin to migrate to the topically applied composition where it absorbed or adsorbed by the silica deposited on the skin from the compositions of the invention. That silica itself should be effective in the treatment of acne and related disorders is highly unexpected in view of the known inert nature of silica. I believe that, in the case of some forms of the silica, the fluid is absorbed by the silica as water of hydration and/or combination, for example in the case of silica gel. However, in other cases, the fluid is adsorbed within the inter-particle interstices of the deposit of silica particles on the skin due to capillary action. This latter mechanism has never been proposed before to remove fluid from acne affected areas of the skin and reduces the risk that the compositions of the invention are rendered less effective due to absorption of water from the atmosphere as opposed to the underlying skin. It is within the scope of the present invention to use mixtures of silica which act both by absorption of fluid as water of hydration or combination and by adsorption of fluid by capillary action.

The silica is preferably used in a form which maximises the capillary action of the silica on the underlying skin to which it is to be applied, and this is conveniently achieved by the use of a fine particulate form, of the silica, notably that with an average primary particle size of less than 10 micrometers, notably less than 5 micrometers. A particularly preferred form of silica for present use is fumed silica which has an average primary particle size of less than 0.1 micrometer. Such fine particle size silica is available commercially and may be used in its commercially available forms in the present invention.

It may be desired to treat the surface of the silica particles to render them more easily wet by the fluid removed from the skin. Such surface treatment includes at least partial coating of the silica particles with a polar material, for example a short chain alkylamine, notably mono- or di-ethylamine, or with a surface active agent. Typical surface active agents include anionic surfactants such as alkarylsulphonates, non-ionic surfactants such as long chain alkane glycols or polyalkylene glycols, notably polyethylene glycols. Such surface treatments of the silica particles can be achieved, for example, by milling the particles and surfactant together, for example in an air mill or a ball mill. The pre-treatment may also reduce the tendency of the silica particles to agglomerate before they are incorporated into the compositions of the invention. The amount of surfactant required to provide satisfactory pre-treatment of the silica particles can be readily established by simple trial and error tests, but will typically be in the range 0.1 to 5% by weight of the silica. If desired, the surfactant can be put up in part of the alkanol, glycol or other fluid carrier to be used in the preparation of the composition of the invention to form a slurry of the pre-treated silica for storage and transport prior to use in the preparation of the compositions of the invention.

In use, the composition of the invention is applied to the affected area of the skin and allowed to dry, if put up in a fluid carrier medium. The resultant silica deposit containing the absorbed or adsorbed secretion from the skin can be removed from the skin as a solid. Alternatively, the deposit can remain upon the skin as an ingredient in a dermatologically acceptable cosmetic composition. It is therefore preferred to put the silica up in a carrier which readily dries upon the skin so as to minimise the formation of greasy deposits upon the skin or in the underlying epidermal layers. Preferably, the silica is put un in a non-oleaginous carrier, notably one which readily vaporises at skin temperature. The use of a volatile carrier for the silica particles also aids formation of fine passages or interstices in the silica deposit on the skin formed when the carrier volatilises from the composition which I believe assists the capillary action of the silica deposit on the skin. Preferred carriers for the silica are thus short chain aliphatic alcohols or glycols, notably those containing from 1 to 4 carbon atoms. Where the alcohol or glycol contains more than 2 carbon atoms, it is preferred to use branched chain materials, for example iso-propyl alcohol. Other carriers which may be used are dermatologically acceptable esters or ketones in which the alkyl moieties contain from 1 to 4 carbon atoms, for example ethyl acetate or acetone, and mixtures of the above carriers with themselves or other dermatologically acceptable ingredients. However, the use of ethanol, for example in the form of surgical spirit, denatured alcohol or methylated spirits, is particularly preferred since it rapidly evaporates from the skin and aids the formation of a deposit of silica which is closely adherent to the skin and thus aids migration of fluid from within the skin.

Mixtures of carriers with other materials may be used; for example with rheological modifiers or suspension stabilisers, for example polyalkylene glycols, polyalkylene ether glycols or cellulose derivatives, and acrylic acid polymers such as the acrylate polymers sold under the Registered Trade Mark Carbopol; moisturising agents, such as urea; and diluents or emulsifying agents where the carrier is in the form of a non-aqueous emulsion, may also be used.

The compositions may thus be put up in the form of a substantially odourless suspension of silica particles in an alcohol carrier, typically as a thick paste, gel or slurry containing from 2 to 50%, preferably 5 to 25%, notably 7.5 to 20% by dry weight of silica. However, it will usually be desired to incorporate one or more fragrances, opacifying agents and other cosmetic ingredients into the composition so that it provides a cosmetic effect when applied to the skin in order to mask the residual silica particles upon the surface of the skin. Thus, the composition can be put up in a conventional non-aqueous foundation cream or gel composition, or can be put up in a solid gel stick or powder composition. Such compositions can, apart from the presence of the silica particles, be of conventional composition. However, as stated above, it is preferred to put the composition up in a volatile fluid carrier medium which evaporates to form the fine passages or interstices in the silica deposit on the skin.

The composition of the invention is applied to the area of the skin which is affected by the acne or similar disorder. The amount of the composition applied will depend upon the extent and severity of the acne, but will typically apply from 10 to 500, preferably 20 to 200, milligrams of silica particles per square cm of the skin. If needed, the application can be repeated as required to eliminate the acne, for example at four hourly intervals. In severe cases, the composition may be applied to a solid carrier, for example a self adhesive plaster, bandage or the like, which is applied to the skin and left in place for a prolonged period. The use of a solid application vehicle to retain the compositions upon the skin may also be desirable where the compositions contain highly deliquescent forms of silica and it is desired to prevent excessive acquisition of moisture by the silica from the environment as opposed to absorption of fluid from the skin.

I have found that the composition of the invention is surprisingly effective in the treatment of the symptoms of acne and that other medical treatment may not be required. The silica may therefore be the sole dermatologically active ingredient in the composition. I believe that the removal of fluid from the affected area of the skin also reduces the activity of bacteria within the affected areas. However, if desired other active ingredients, for example medicaments, eg. anti-biotics, anti-bacterials, retinoids and/or benzoyl peroxide, may be incorporated in the compositions of the invention and/or may be applied to the affected area in a separate treatment. Furthermore, the compositions of the invention may also find use in the treatment of inflamed areas of the skin which are caused by other mechanisms than the activity of the sebaceous glands, for example inflamed areas around hair follicles, and the term related disorders is used herein to denote disorders of the skin which exhibit the same type of symptoms as acne itself.

Following the application of the composition of the invention to the affected area, fluid from the underlying skin migrates the silica particles, at a rate which I believe is greater than that at which the skin can replenish the skin fluids, to form a slightly dampened powder deposit upon the skin. This can be removed by brushing or by washing the skin, preferably after a period of from 5 to 60 minutes; or can be allowed to remain upon the skin to continue to absorb fluid from the skin, notably where the silica particles are incorporated in a cosmetic composition such as a foundation cream or powder. As indicated above, we have found that the use of a volatile alcohol, ketone or ester as the carrier for the silica particles aids drying of the composition on the skin and the absorption and/or adsorption of fluid from the skin by the silica particles.

The compositions of the invention can be made by any suitable method, for example by milling the components together. If desired, the compositions can be made by mixing some or all of the ingredients in a high speed mixer, for example a high shear mixer, to form a stable viscous gel or paste of the solid particles in the fluid carrier medium. However, we have found that problems can arise if excessive shear working of the composition is carried out. The optimum amount of such shear working of the composition will depend upon the nature and relative proportions of the ingredients and can readily be established by simple trial and error tests.

The invention thus also provides a method of making a composition of the invention which comprises mixing the ingredients of the composition together.

The invention will now be illustrated by the following Examples in which all parts and percentages are by weight unless stated otherwise:

EXAMPLE 1

A composition was prepared by mixing fine aerogel silica particles with just sufficient surgical spirit to form a viscous paste containing approximately 50 parts of silica and 50 parts of surgical spirit. The paste was applied as a thick coating to the acne spots of a sixteen year old girl suffering from acne. The alcohol rapidly evaporated from the coating of paste applied to the skin and formed a powdery residue upon the skin. After 30 minutes this residue was washed off the skin and the acne spots examined. It was noted that the spots had diminished in size and redness to the point where they were not embarrassingly visible. The treatment was repeated on a daily basis and it was noted that the acne spots virtually disappeared after three days. It was also noted that the treatment did not cause excessive drying, cracking or chaffing of the skin which would have been expected if the sole action of the silica was as a desiccant.

EXAMPLE 2

A white viscous gel was made by shear mixing 10 parts of fine powdered silica with a particle size of less 5 micrometres with 90 parts of ethanol and the gel was filled into 40 gm capacity aluminium tubes.

The gel was applied to the faces of 20 patients, 11 male and 9 female aged between 18 and 35 and suffering facial pimples. The gel was applied to the pimple itself and the surrounding skin area to apply approximately 1 to 2 g of the gel to an area of about 1 to 4 square cms. The gel was allowed to dry and left on the skin for a period of 60 minutes. The powdery deposit was washed off the skin and the status of the pimples re-examined after a further 4–6 and 12–18 hours (visits 2, 2 and 3). The pimples were assessed by the investigator in terms of erythema, oedema and size and by the patient for redness and swelling.

The total oedema score for the whole group of patients fell from 28 at 1 hour after application of the gel (visit 1), to 25 at visit 2 and 14 at visit 3. The total erythema score for the whole group fell from 28 at visit 1 to 24 at visit 2 and 20 at visit 3. The redness score assessed by the patients fell from an average score of 20 at visit 2 to 5 at visit 3 and 14 patients reported no redness at visit 3. The swelling scores assessed by the patients fell from and average score of 8 at visit 2 to 5 and 17 patients reported no swelling at visit 3.

The patients reported good acceptance with little stinging or burning sensation caused by the gel and the overall inflammation of the skin at the pimples was markedly reduced.

Whilst the invention has been described above in terms of the treatment of acne spots, it may also be applied in other conditions where it is desired to reduce the secretion of excessive fluid in the skin and in the treatment of such conditions in mammals other than humans.

What is claimed is:

1. A substantially non-aqueous dermatologically active composition suitable for topical application to the skin of a mammal suffering from acne or related disorders of the skin, said composition consisting essentially of the following ingredients:
   (a) at least 5% by weight of a particulate anhydrous silica or a precursor thereof having a primary particle size less than 10 micrometers for treating acne or related skin disorders, said particulate anhydrous silica or the precursor thereof being the dermatologically active ingredient of said composition; and
   (b) a substantially non-aqueous carrier medium for said particulate silica comprising a volatile solvent selected from alkanols, alkyl glycols, alkyl ketones and/or alkyl esters in which the alkyl moieties contain from 1 to 4 carbon atoms.

2. A composition as claimed in claim 1, wherein said composition contains up to 50% by dry weight of the silica.

3. A composition as claimed in claim 1, wherein said composition comprises from 7.5 to 25% by weight of the silica.

4. A composition as claimed in claim 1, wherein the carrier medium is ethanol.

5. A composition as claimed in claim 1, wherein said composition is put up as a cosmetic composition.

6. A composition as claimed in claim 1, wherein said composition is a viscous gel or paste.

7. A composition as claimed in claim 6, wherein said composition contains a rheological modifier and/or a suspension or dispersion stabilizer.

8. A composition according to claim 1, wherein the particles of the silica have been treated to render them more readily wet by skin fluids.

9. A method for the alleviation of the symptoms of acne and related skin disorders in mammals, which method comprises applying to the affected area of the skin of the mammal a dermatologically effective amount of a substantially non-aqueous composition consisting essentially of:
   a. at least 5% by weight of a particulate anhydrous silica or a precursor thereof having a primary particle size less than 10 micrometers for treating acne and related skin disorders; and
   b. a substantially non-aqueous liquid carrier medium for said particulate silica comprising a volatile solvent selected from one or more alkanols, alkyl glycols, alkyl ketones and/or alkyl esters in which the alkyl moieties contain from 1 to 4 carbon atoms.

10. A method as claimed in claim 9, wherein the composition contains up to 50% by dry weight of the silica.

11. A method as claimed in claim 9, wherein the carrier medium evaporates from the composition applied to the skin to form a deposit of silica particles upon the skin, which deposit contains fine passages or interstices which exert a capillary action upon the underlying skin to remove fluid from the skin.

12. A method as claimed in claim 9, wherein the step of applying the silica or a precursor thereof comprises applying from 10 to 500 milligrams of silica particles per square cm of skin.

13. A method as claimed in claim 9, and further comprising the step of allowing the composition to dry and remain on the skin.

* * * * *